(12) United States Patent
Brunner

(10) Patent No.: US 9,024,624 B2
(45) Date of Patent: May 5, 2015

(54) MULTI-FIELD MAGNETIC TRACKING

(75) Inventor: Georg Brunner, Constance (DE)

(73) Assignee: Northern Digital Inc., Waterloo, Ontario (CA)

( * ) Notice: Subject to any disclaimer, the term of this patent is extended or adjusted under 35 U.S.C. 154(b) by 830 days.

(21) Appl. No.: 13/044,720

(22) Filed: Mar. 10, 2011

(65) Prior Publication Data

US 2011/0224537 A1   Sep. 15, 2011

Related U.S. Application Data

(60) Provisional application No. 61/312,577, filed on Mar. 10, 2010.

(51) Int. Cl.
*G01B 7/14* (2006.01)
*A61B 5/06* (2006.01)

(52) U.S. Cl.
CPC ...................................... *A61B 5/062* (2013.01)

(58) Field of Classification Search
CPC ...... G01D 5/145; G01D 5/204; G01D 5/2066
USPC ....................................... 324/207.15, 207.16
See application file for complete search history.

(56) References Cited

U.S. PATENT DOCUMENTS

| 6,246,231 | B1 | 6/2001 | Ashe |
| 6,528,991 | B2 | 3/2003 | Ashe |
| 6,784,660 | B2 | 8/2004 | Ashe |
| 8,446,147 | B2 * | 5/2013 | Chiba et al. ............... 324/207.15 |
| 2010/0324412 | A1 * | 12/2010 | Govari et al. ................. 600/424 |

FOREIGN PATENT DOCUMENTS

| CN | 1168625 | 12/1997 |
| CN | 1459030 | 11/2003 |
| CN | 101028188 | 9/2007 |
| CN | 101396266 | 4/2009 |

* cited by examiner

*Primary Examiner* — Reena Aurora
(74) *Attorney, Agent, or Firm* — Fish & Richardson P.C.

(57) ABSTRACT

A magnetic tracking system includes a first set of magnetic field generators configured to produce a first magnetic field having a first shape within a three dimensional region and at least a second set of magnetic field generators configured to produce a second magnetic field having a second shape within the three dimensional region. The system also includes a computing device configured to compute a position of a sensor within the three dimensional region based on the first and second magnetic fields being detected by the sensor.

20 Claims, 11 Drawing Sheets

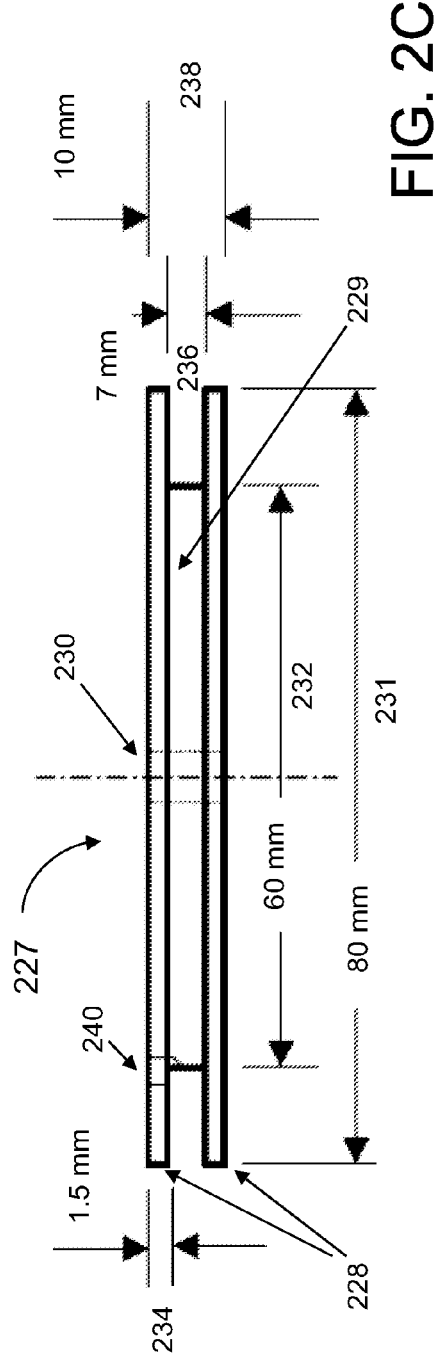
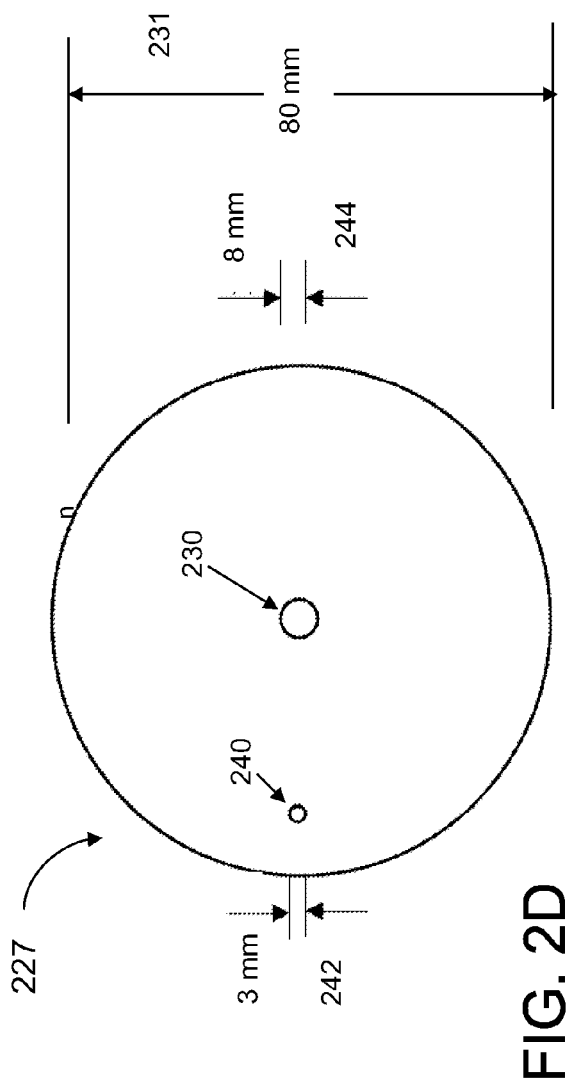
FIG. 2C
FIG. 2D

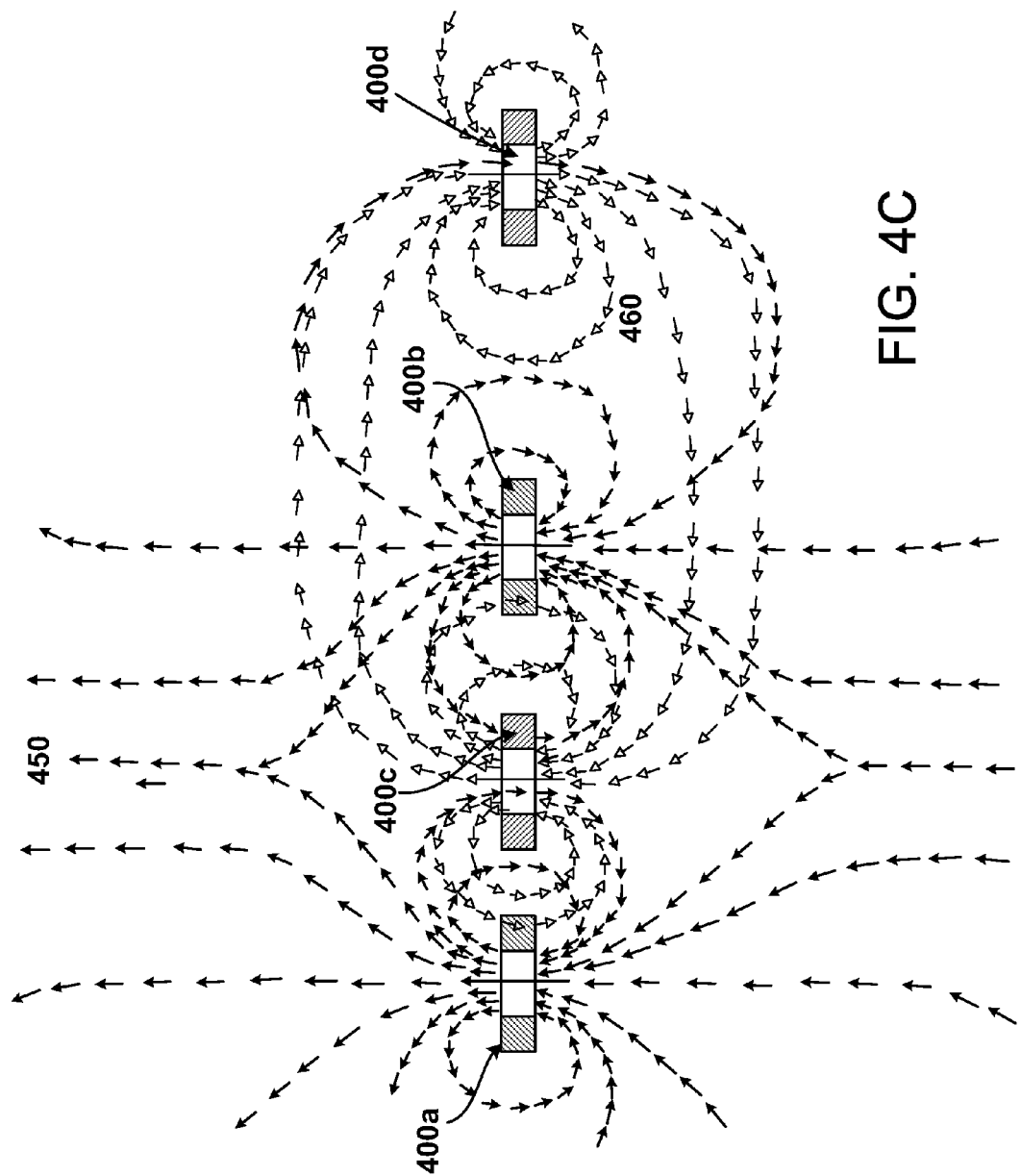

MULTI-FIELD MAGNETIC TRACKING

RELATED APPLICATIONS

This application claims priority to U.S. Provisional application 61/312,577, filed on Mar. 10, 2010, the entire content of which is incorporated herein by reference.

In addition, the present application is related to the following United States applications: application Ser. No. 09/544,539 filed Apr. 7, 2000, now U.S. Pat. No. 6,553,326, issued Apr. 22, 2003; application Ser. No. 09/892,153, filed Jun. 26, 2001, now U.S. Pat. No. 6,625,563, issued Sep. 23, 2003; application Ser. No. 10/333,828, filed Apr. 14, 2003, now U.S. Pat. No. 6,836,745, issued Dec. 28, 2004; and application Ser. No. 10/824,846, filed Apr. 15, 2004, now U.S. Pat. No. 7,783,441, issued Aug. 24, 2010, the complete disclosures of all of which are incorporated herein by reference.

TECHNICAL FIELD

This disclosure relates to use of magnetic fields for determining an object's location and orientation.

BACKGROUND

Magnetic tracking systems use magnetic fields to determine the location and orientation of an object within a given region. A sensor is positioned on the object (e.g., a piece of equipment or a human body) to detect magnetic fields present within the given region. From the detected field information, a computer system may compute the location and orientation of the object with respect to a reference coordinate system. These systems are useful, for example, in the medical field, for tracking instruments associated with medical procedures thereby facilitating advanced methods in surgery and diagnostics.

SUMMARY

In one aspect, a magnetic tracking system includes a first set of magnetic field generators configured to produce a first magnetic field having a first shape within a three dimensional region and at least a second set of magnetic field generators configured to produce a second magnetic field having a second shape within the three dimensional region. The system also includes a computing device configured to compute a position of a sensor within the three dimensional region based on the first and second magnetic fields being detected by the sensor.

In another aspect, a magnetic tracking system includes a field generator assembly generating a plurality of magnetic fields wherein each field is generated by a set of at least two magnetic field generators. The system also includes a magnetic sensor to measure the plurality of magnetic fields and a computing device configured to compute a position and orientation of the magnetic sensor within the magnetic fields being measured by the sensor.

In another aspect, an apparatus includes a structural surface for supporting a portion of a patient during a medical procedure. The apparatus also includes a surface that includes a plurality of simultaneously activated magnetic field generators sets for producing magnetic fields to form a measurement volume.

In another aspect a method includes activating a first set of magnetic field generators to produce a first magnetic field having a first shape within a three dimensional region, and activating a second set of magnetic field generators to produce a second magnetic field having a second shape within the three dimensional region. The method also includes determining, a position of a sensor within the three dimensional region based on detecting the first and second magnetic fields by the sensor Implementations may include one or more of the following. The field generators from the first set can be excited simultaneously to produce the first magnetic field. The field generators from the second set can also be excited simultaneously to produce the second magnetic field. The system can include additional sets of magnetic field generators. For example, at least a third set of two or more magnetic field generators can be configured to operate together to form a third magnetic field having a third shape within the three dimensional region. Similarly, a fourth and fifth sets, each set comprising two or more magnetic field generators can be configured to operate together to form a fourth and fifth magnetic fields, respectively, within the three dimensional region. The computing device can compute the position of the sensor based on the sensor detecting one or more of the third, fourth and fifth magnetic field.

Each of the first, second and third sets can include two or more magnetic field generators. The first set of magnetic field generators can be activated during a first time period and the second set of magnetic field generators can be activated during a second time period, different from the first time period. The first and second sets of magnetic field generators can be active during a first time period. The first set of magnetic field generators can operate at a first frequency and the second set of magnetic field generators can operate at a second frequency, different from the first frequency. A magnetic field induced by a magnetic field generator in a set can be parallel or anti-parallel to a magnetic field generated by at least another magnetic field generator in the same set.

The magnetic field generators can include electromagnetic coils. The magnetic field generators can be positioned on a plane. A portion of the magnetic fields generated by the field assembly can be parallel in direction. A portion of the magnetic fields generated by the field assembly have different amounts of magnetic flux. An Eddy current can be a source for one of the at least two magnetic field generators. One of the at least two magnetic field generators can include a magnetic material The apparatus can include an electrically conductive layer positioned below the surface that includes the plurality of activated magnetic field generators sets.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 2C and 2D are lateral and top views, respectively, of an example of a magnetic field generator.

FIGS. 4A, 4B and 4C are schematic diagrams showing examples of magnetic fields induced by sets of magnetic field generators.

Like reference symbols in the various drawings indicate like elements.

DETAILED DESCRIPTION

Figure 1:
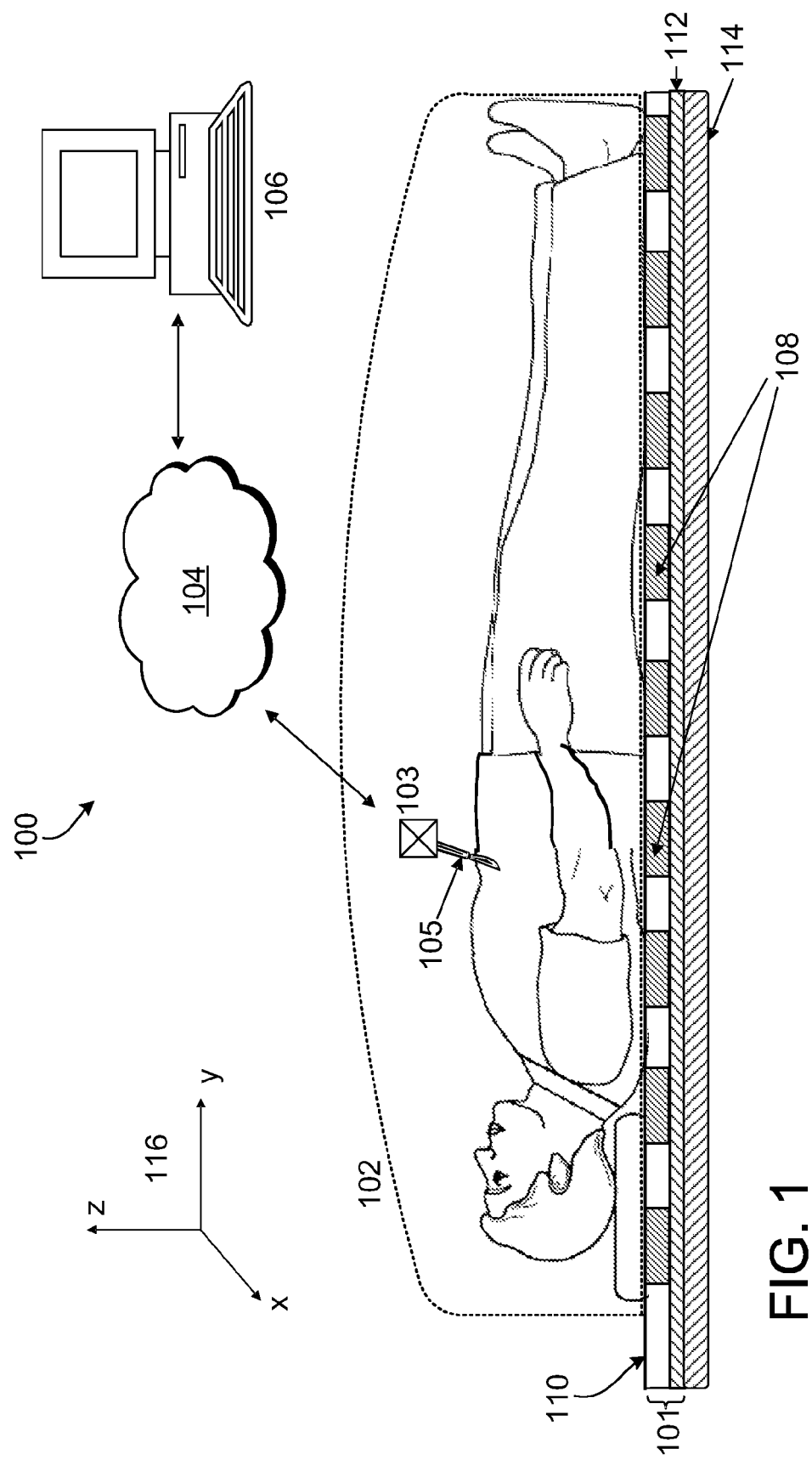
FIG. 1 is a schematic diagram of a magnetic tracking system.

Referring to FIG. 1, a schematic diagram of a magnetic tracking system 100 is shown and described. In brief overview, the system 100 includes a magnetic field generating assembly 101 that is configured to generate magnetic fields within a given volume or three dimensional region 102. A sensor assembly 103 placed on an object 105 (e.g. a scalpel) within the given volume 102 detects and/or measures the magnetic fields and communicates the measurements to a computing device 106, in this particular example, by way of a communications link 104 (e.g. wired or wireless connections). Based on the measurements by the sensor assembly 103, the computing device 106 can compute a position of the sensor assembly 103 (and therefore of the object 105) with respect to a coordinate system 116. Such position computation facilitates motion tracking of the sensor assembly 103 within the region 102. This is useful in advanced surgical procedures where the sensor assembly 103 can be mounted on objects 105 such as a scalpel to track the motion of the objects as a medical procedure is being executed (e.g., track the movements of the scalpel with relation to a reference such as a second sensor assembly fixed to the body of a patient).

In some implementations, the field generating assembly 101 is relatively thin in dimensions (e.g., height) and can be mounted on a flat surface such as a surgical table 114. Such a field generating assembly may be referred to as a flat field generator. Even though FIG. 1 depicts the field generating assembly 101 as being mounted on the surgical table 114, in some implementations, the field generating assembly 101 may be integrated into the surgical table 114 by possibly embedding the field generating assembly 101 within the surgical table 114. In this particular arrangement, the field generating assembly 101 includes a plurality of field generators 108 that each may include one or more electromagnetic coils that locally induce a magnetic field (e.g., by passing current through each coil). Typically, an electromagnetic coil is formed by winding a conductor, such as an electrical wire, around a core of magnetic material or a non-magnetic material (e.g., air). When a current is passed through the windings of a coil, a magnetic field that develops extends through the center of the coil along its longitudinal axis and circles back around the outside of the loop or coil. The magnetic field circling each loop or winding of wire combines with the fields from the other loops to produce a concentrated field down the center of the coil. The strength of a coil's magnetic field can be controlled by controlling the introduced current, the number of loops or windings of the coil, and other parameters and characteristics associated with the coils.

In some implementations, the shape of induced magnetic fields can be controlled by exciting one or more field generators 108 at the same time. For example, when a single coil or field generator 108 is excited, a dipole magnetic field is induced in the volume 102. In some implementations, multipole fields may be induced by exciting multiple field generators 108 at the same time. In general, the shape of the induced field can be varied based on different parameters. In some implementations, the shape of the induced magnetic field can be varied based on the number of field generators that are simultaneously activated. For example, two, three, four or more field generators can be activated or excited simultaneously to control the shape of the induced magnetic field.

Relative spatial distribution of the simultaneously activated field generators 108 may also factor into shaping the induced field. For example, when three field generators 108 are activated simultaneously, the induced magnetic field is typically different when the three field generators 108 are in a straight line as opposed to when they are each positioned at a vertex of a triangle, for example. In the example shown in FIG. 1, the generators 108 are shown to be substantially positioned on a same plane. However, the generators 108 may be positioned based upon other spatial distributions in three dimensional space without deviating from the scope of this application. For example, in some implementations, a set of generators 108 may be distributed below the patient (as shown) while another set of generators may be distributed above the patient. In some implementations, the positions of the field generators 108 can be made adjustable. For example, the field generators 108 can be made movable along a pre-defined channel or path such that their absolute and/or relative positions within the field generating assembly 101 can be adjusted to manipulate the shapes of the induced fields. In some implementations, a field generator 108 can also be made rotatable with respect to a point either on or external to the field generator 108. For example, the field generators 108 can be disposed in the field generator assembly 101 such that angles between the horizontal and the top surface of the individual field generators are individually configurable. One or more modular designs may be used for positioning field generators, for example, generators may be added, removed and interchanged in a modular fashion to form patterns for producing one or more measurement zones from the correspondingly generated fields.

In some implementations, the shape of the field can also be controlled by controlling the direction of current flowing through the field generators 108. For example, a pair of generators 108 can be simultaneously activated such that the direction of current flow is equivalent for both generators and hence their respective induced fields can be considered to be parallel with each other. Alternatively, the direction of current flow in a pair of simultaneously activated field generators can be opposite to each other thereby inducing fields that can be considered anti-parallel. A variety of shapes can therefore be created by using different combinations of parallel and anti-parallel fields induced by individual generators when more than two generators are simultaneously activated. Other parameters may be varied in that pair of simultaneously activated generators 108 (along with individual generators) to control the shape of the induced fields. For example, level of current flowing through the individual generators, number of windings in the individual generators, physical dimensions of the generators, materials used to construct the generators, and other similar parameters used for shape control. In some implementations, coils with adjustable taps can be used to control the number of windings of a field generator 108.

In some implementations, the presence of particular types of materials (e.g., conductive materials) in the vicinity of the induced magnetic fields may contribute to distorting or changing the shape of the fields. Even due to the presence of permeable materials, the shape of the fields may bend or change. In general, random presences of conductive and/or permeable objects generate parasitic eddy current fields, thereby distorting the shape of the induced fields. While a random presence of such conductive and/or permeable materials is usually not desirable, in some implementations, such objects may be used for controlling the shape of the induced magnetic fields. For example, a conductive plate 112 can be used to shield or shape the induced magnetic fields. In the illustrated example, it is not desirable to have the induced magnetic fields below the plane of the field generator assembly 101. In such cases, the conductive plate or shield 112 significantly attenuates the magnetic field located below the field generator assembly 101 thereby making the system insensitive to objects (e.g. metallic or permeable objects) positioned below the field generator assembly 101.

In some implementations, the field generator assembly 101 also includes a covering layer 110 that substantially encases the field generators 108. The covering layer 110 provides an interface surface for the patient (e.g., to sit or lie on) during a procedure. The covering layer 110 may be constructed from various types of material or material combinations, for example, a non-conductive or non-magnetic material such as plastic may be incorporated into the covering layer 110. In some implementations, the covering layer 110 can be configured to provide mechanical support to the field generators 108. For example, the field generators 108 can be embedded within a solid covering layer 110. In some implementations, the layer 110 can simply cover the field generators 108. In some implementations, where the field generators 108 are movable, the covering layer 110 can be constructed to accommodate the possible motions (e.g. translational, rotational, etc.) or module combinations of the field generators. For example, the channels or paths for the movable field generators can be defined in the covering layer 110.

The sensor assembly 103 is used to detect the magnetic fields induced in the region 102. In some implementations, the sensor assembly 103 may include one or multiple sensors (e.g., a sensor array) that incorporate one or more types of sensing technology. For example, the sensor assembly 103 may include a simple coil, several coils, one or more Hall sensors, a flux gate sensor or other types of sensors capable for measuring characteristics of an electromagnetic field (e.g., magnetic field flux, magnetic field differential etc.). In some implementations, magnetic fields generated by one or more field generators 108 induce electromotive forces (EMF's) in the sensor assembly 103. The measured EMF's represent the measured local values of magnetic fields at the location and orientation of the sensor assembly 103 in a three dimensional space that defines the region 102. In some implementations, the sensor assembly 103 includes multiple sensors, such as two distinct sensor coils, thereby potentially doubling the number of individual field measurements achievable by the sensor assembly 103. In some implementations, the sensor assembly 103 may include additional components (e.g., circuitry, electronics devices, etc.) for communicating the measured signals to a computing device 106. For example, the sensor assembly 103 may include a transceiver configured to communicate with the computing device 106 (for example, by way of the communications link 104 which can include simple wired or wireless connections or may utilize a wired or wireless network).

Typically, the sensor assembly 103 outputs signals that represent several measured magnetic fields corresponding to the individual fields induced by activating different sets (e.g., pairs) of field generators 108. Measuring several fields induced within the region 102 allows tracking of the sensor assembly 103 with multiple degrees of freedom. For example, at least five different magnetic fields may be used to determine five degrees of freedom (x, y, z, $\phi$, $\theta$), where the coordinates (x, y, z) and angles ($\phi$, $\theta$) specify the three-dimensional location and orientation, respectively, of the sensor with respect to a reference. In some implementations, higher number of fields can improve the accuracy in calculating the location of the sensor assembly 103. For example, the field generator assembly 101 can be configured such that eight different sets of field generators 108 are used for inducing the distinct magnetic fields. In this configuration, the sensor assembly 103 would measure the respective fields generated by each of the eight sets of field generators 108, resulting in eight distinct field measurements.

In some implementations, where the sensor assembly 103 includes two sensor coils, each coil could independently measure the strength of the magnetic field generated by a single set of field generators. Therefore, if eight distinct field measurements are desired and the sensor assembly 103 includes two sensor coils, only four sets of field generators 108 would be needed, as each coil would independently measure the field generated by each of the four sets of field generators 108, thus resulting in eight distinct field measurements.

In other implementations, where the sensor assembly 103 includes two or more sensor coils, the coils could be treated as a set. Such a set would allow the sensor coils to be positioned and oriented to optimize the measurement of the magnetic field.

In some implementations, the measured magnetic field values depend on one or more system related parameters (e.g., a gain factor of the sensor assembly 103) and the three-dimensional location and the orientation of the sensor coil. The number of sets of field generators 108 and the number of sensor coils in the sensor assembly 103 may vary depending upon number of factors including the particular measurement application (e.g., measurements in a surgical theater). In this particular arrangement, the computing device 106 determines the gain factor of the sensor assembly 103 along with the position and orientation of the sensor assembly 103. Since the position and orientation of the sensor assembly 103 is described by specifying multiple degrees of freedom (e.g. up to six degrees that include x-axis position, y-axis position, z-axis position, roll, pitch, and yaw), a matching number of position factors (e.g., six) may be calculated by the computing device 106. As such, the computing device 106 produces a combined number of factors (e.g., seven) for representing the position and gain. In some implementations, the number of distinct field measurements desired to determine these factors is one greater than the number of factors being determined. Accordingly, if the computing device 106 determines the system gain factor and six positional factors (i.e., degrees of freedom), i.e. a total of seven calculated factors, a total of eight distinct field measurements may be needed. As stated above, this can be achieved utilizing a single sensor coil in the sensor assembly 103 and eight sets of field generators 108. Alternatively, a sensor assembly with two sensor coils and four sets of field generators 108, or other similar variations, may be utilized. Similarly, if the computing device 106 determines the system gain factor plus five positional factors (i.e., five degrees of freedom), a total of six calculated factors need to be determined. Again, as described above, this can be accomplished utilizing a variety of configurations of the field generator sets and sensor coils.

Figure 3A:
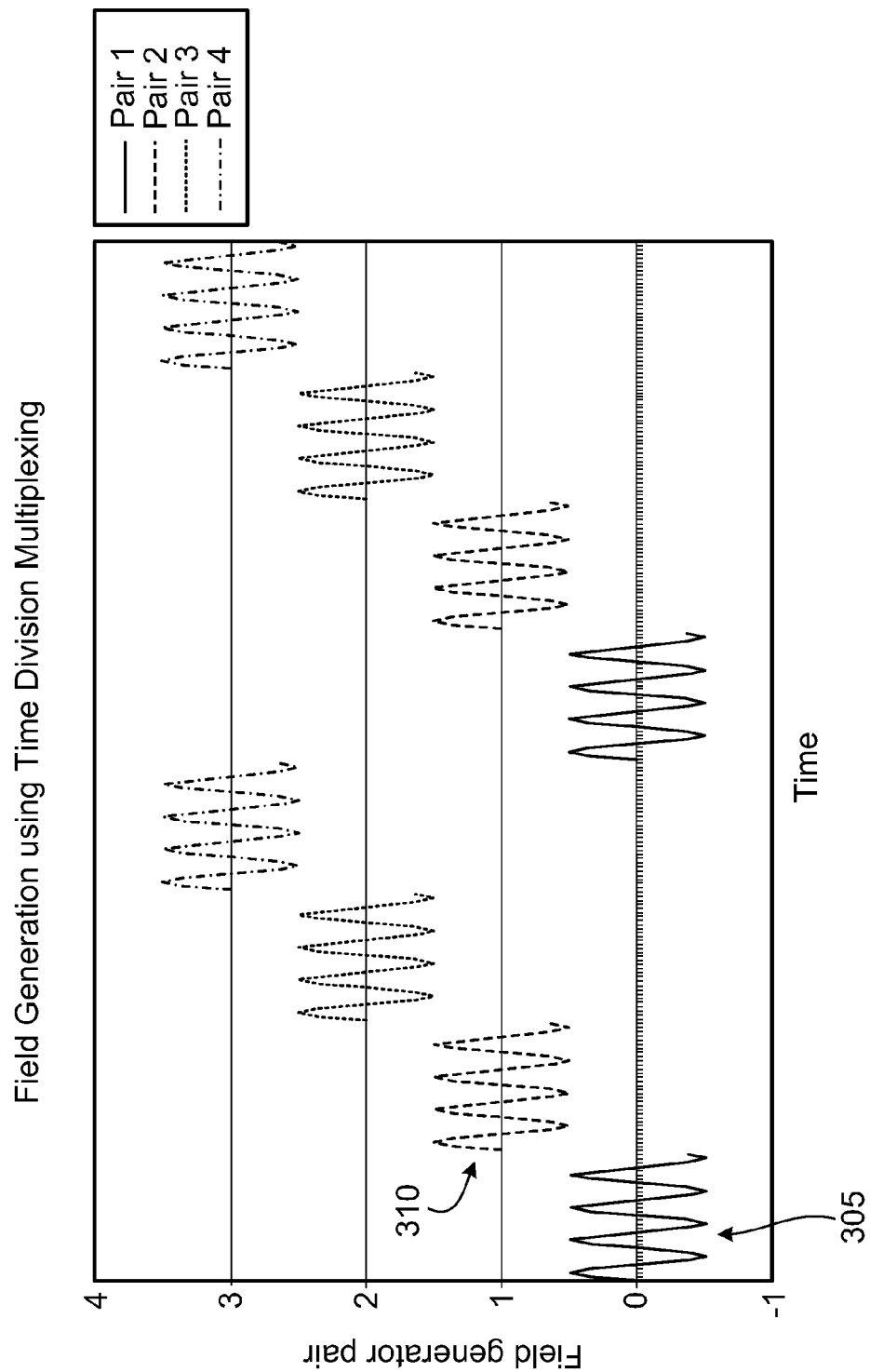
FIG. 3A shows an example of a time division multiplexed scheme of exciting different sets of magnetic field generators.

When different sets of field generators 108 are excited during separate time instances, the computing device 106 may need to know details about the field generators inducing the detected magnetic fields. In one arrangement, the computing device 106 can identify the set of field generators 108 inducing the magnetic field detected by the sensor assembly 103 based on information communicated to the computing device 106 from the field generator assembly 101. In other implementations, the timing of the field generators and the sensor assembly is derived from a synchronization signal derived from one of: the computing device, the field generator assembly, or the sensor assembly. In some implementations timing information related to the induced fields is used to identify the set of field generators 108 producing a measured field. For example, field generator assembly 101 may temporally multiplex power to the different field generators 108 and provide the timing information for determining the location of the sensor assembly 103 (e.g., the information is provided to the computing device 106 via the sensor assembly 103 and the communications link 104). An example of such a time division multiplexed scheme is shown in FIG. 3A. In this example, a short pulse of alternating current 305 is used to excite one generator pair included in the generators 108 (represented as pair 1 in the legend) at a given time instant. The duration of the pulse may be relatively short (e.g., on the order of a millisecond) and once complete, another pair of generators (represented as pair 2 in the legend) may be activated with a substantially similar pulse 310. The process is repeated for other pairs in a way that not more than one generator set (e.g., pair) is excited during a given time interval. Information representing the timing and activations of the generator sets that may be provided (e.g., to the computing device 106) include, for example, the starting point of a current pulse, the duration of a current pulse, the end point of a current pulse, order and identity of the generator sets being excited by the current pulse, etc.

Figure 3B:
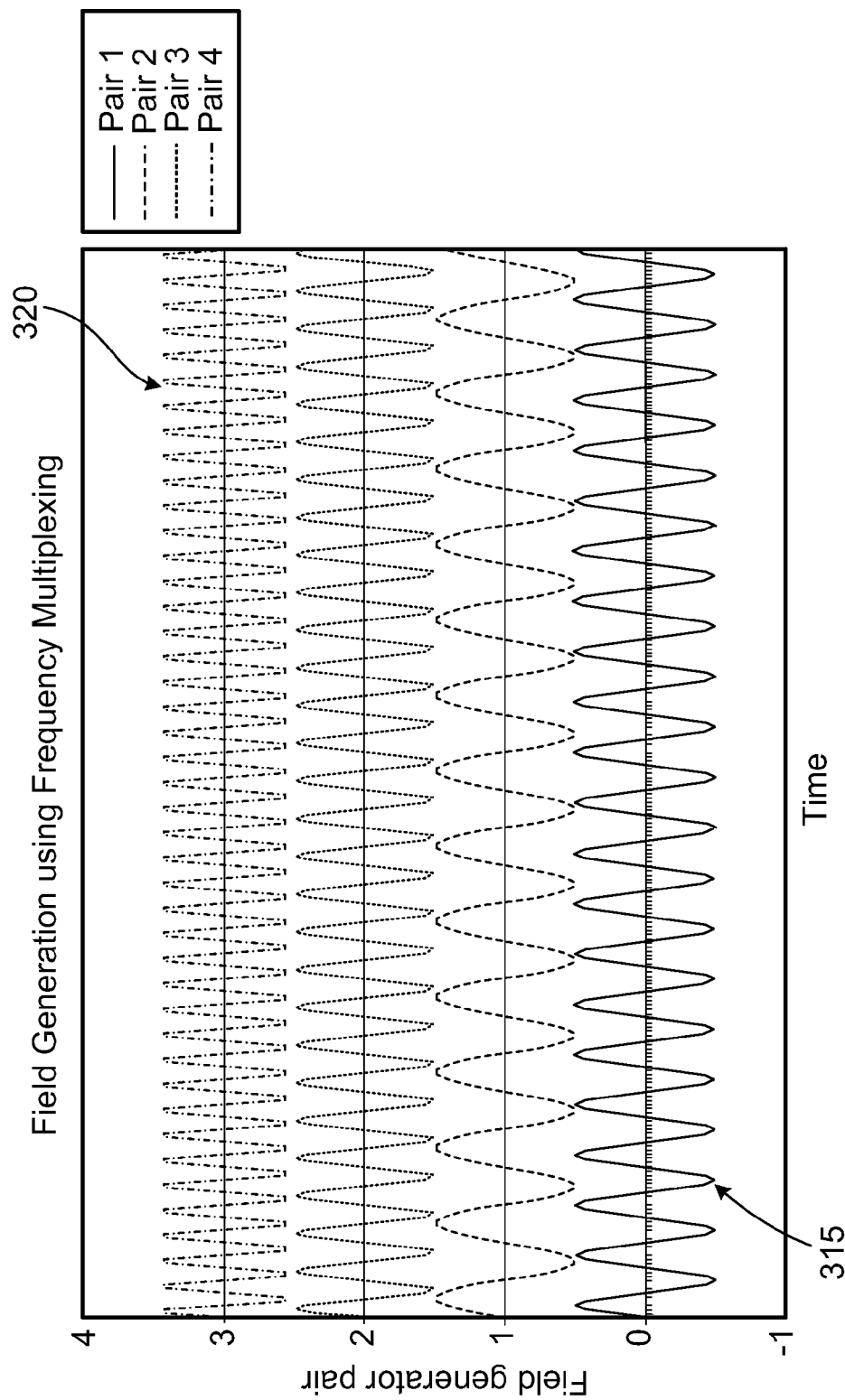
FIG. 3B shows an example of a frequency division multiplexed scheme of exciting different sets of magnetic field generators.

In some arrangements, the field generating assembly 101 may drive each set of field generators 108 at different frequencies. To identify the particular set of field generators responsible for a measured field, the computing device 106 may decompose measured EMF's from the sensor assembly 103 into frequency components. These frequency components of the measured fields are then matched to individual sets of field generators. An example of such a frequency division multiplexed excitation scheme is shown in FIG. 3B. In this example, a given set of generators (e.g., pair 1 as represented on the legend) is excited by an alternating current 315 at a first frequency. Another set of generators (e.g., pair 4) is also excited at the same time by another alternating current 320 that has a second frequency, which is different from the first frequency. Similarly, the other sets of generators may be excited using alternating currents operating at other frequencies.

The sensor assembly 103 sends the measured field values to the computing device 106 that uses the measured magnetic field values to determine the location/orientation of the sensor assembly 103. In some implementations, such determinations are executed by comparing the measured magnetic field values to magnetic field values from a physical model.

The physical model can be a set of physical equations that determine values of magnetic fluxes measured by the sensor assembly 103 as a function of several parameters. As such, the physical model may describe the values of magnetic fluxes that can be expected at different points within a measurement volume (such as the region 102) due to magnetic fields induced by known sources at known locations (such as sets of field generators). The parameters can therefore be calculated from an actual measurement by comparing with the physical model. The parameters may include but are not limited to: the position, orientation, and magnetic moments of the set of field generators 108; and the location, orientation, and sensitivity of the sensor assembly 103. A vector (x, y, z) and a pair of angles ($\phi$, $\theta$) may specify the three-dimensional location and orientation of the sensor coil(s) in the sensor assembly 103. If the sensor assembly 103 has multiple coils, the parameters may include an additional angular parameter ($\Psi$) that defines relative orientations of coils in the sensor assembly 103. Such a parameter (e.g., a sixth degree of freedom) may be calculated by utilizing a sensor assembly 103 having a second coil on a different axis (as multiple coils operating on equivalent axes may not allow sensing probe rotation about that axis). The physical model may describe each set of field generators 108 as a magnetic multi-pole such that the fields measured by the sensor assembly 103 are the associated multi-pole fields (e.g., dipole or quadrapole). The multi-pole field values can depend on the system gain and the location, orientation, and magnetic moment "m" of each individual field generator 108. The measured values of the magnetic flux may depend on the location, size, orientation and gain of the sensor assembly with respect to the field generators 108.

In some implementations, the physical model can also be based on one or more underlying assumptions regarding the environment near the region 102. For example, a model may assume pre-selected values for the location and orientation of each set of field generators 108 and the absence of other sources or field distorting objects. The presence of field distorting objects (e.g., conductors, other field sources) may require additional parameters in order for the model to correctly predict field values. In some implementations, the sensor assembly 103 may measure time varying magnetic fields. Alternatively, if static field measurements are desired, a flux gate sensor, hall effect sensor or similar type of sensor can be utilized in the sensor assembly 103 to provide the measurement of static (or constant) magnetic fields. In some implementations, once measured by the senor assembly 103, the magnetic field values are provided to the computing device 106 that calculates the appropriate system gain factor and location/orientation of the sensor assembly 103. In some implementations, the sensor assembly 103 measures a set of magnetic fluxes to obtain a set of measured magnetic field values $B_1$-$B_n$, in which "n" is greater than or equal the number of factors (i.e., position and system gain) being calculated.

In some arrangements, the set of measured field values $B_1$-$B_n$ may have a non-linear dependence on the three-dimensional location/orientation of the sensor assembly 103 and a linear dependence on the system gain factor. The location and orientation of the sensor assembly 103 may be defined by a vector (x, y, z) and at least a pair of azimuthal and polar angles ($\phi$, $\theta$), respectively. The vector (x, y, z) can be specified with respect to a coordinate system 116 with a known origin. While FIG. 1 illustrates a Cartesian coordinate system 116, other types of coordinate systems, such as a polar coordinate system, may be used. Further, the system gain factor of the sensor assembly 103 can be defined by a gain coefficient (g). By using a physical model for the "measured" field dependencies, the computing device 106 can determine the gain factor, location, and orientation of the sensor assembly 103 from the associated set of measured field values $B_1$-$B_n$. In some implementations, the gain factor, location and orientation may be calculated by the computing device 106 via an iterative process. Such an iterative process is described in commonly-owned U.S. application Ser. No. 09/892,153, filed Jun. 26, 2001, which is incorporated here by reference in its entirety.

The physical model may describe a pre-selected magnetic environment in the region of the sensor assembly 103 (e.g., the region 102). The pre-selected magnetic environment may or may not include contributions from nearby objects. For example, the actual environment may be different due to the presence of field distorting objects that support Eddy currents (e.g., a pair of surgical scissors, ferromagnetic materials, and active sources of magnetic fields). If the pre-selected environment is different from the actual environment, the model may require incorporation of additional parameters in order to predict correct magnetic field values. In some implementations, the computing device 106 can be configured to detect and alert users about the presence of potentially measurement distorting conditions (e.g., by flashing messages on a video monitor or through audio alert signals). In some instances, the effects of field distorting objects that support Eddy currents can be reduced by treating these Eddy current sources as additional generators. While the object 105 is shown to be a scalpel in FIG. 1, this is only for illustrative purposes. The object 105 can be other devices or tools e.g., a catheter, an endoscope, biopsy needles, body-mounted position sensors, etc.

The computing device 106 can be any computer, such as a laptop or desktop computer, configured to perform the functions described herein. In some implementations, the computing device 106 is a mobile computing unit such as a smart phone, a personal digital assistant, or a handheld computing unit. In some implementations, the computing device is a specialized computing device designed specific for the purposes of controlling the magnetic field generation, and calculating the position and orientation of the sensor coil from the measured signals. The computing device 106 is configured to run computer program products tangibly embodied in an information carrier, e.g., in a machine-readable storage device, for execution by a programmable processor; and features can be performed by a programmable processor executing a program of instructions to perform functions of the described implementations by operating on input data and generating output. In some implementations, the sensor assembly 103 and the computing device 106 are configured to communicate with each other via communication links such as universal serial bus (USB), Bluetooth, wireless USB etc. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors. Generally, a processor will receive instructions and data from a read-only memory or a random access memory or both. The computing device 106 can include a processor for executing instructions and one or more memories for storing instructions and data.

The computing device 106 may communicate with the sensor assembly 103 over the communications link 104. In some implementations, the communications link 104 may include direct wired or wireless connections between the sensor assembly 103 and the computing device 106. Such connections can include USB, Bluetooth, wireless USB, Firewire etc. In other cases, the communications link 104 may include a wired or wireless network such as a local area network (LAN), a metropolitan area network (MAN) or a wide area network (WAN) such as the Internet.

Figure 2A:
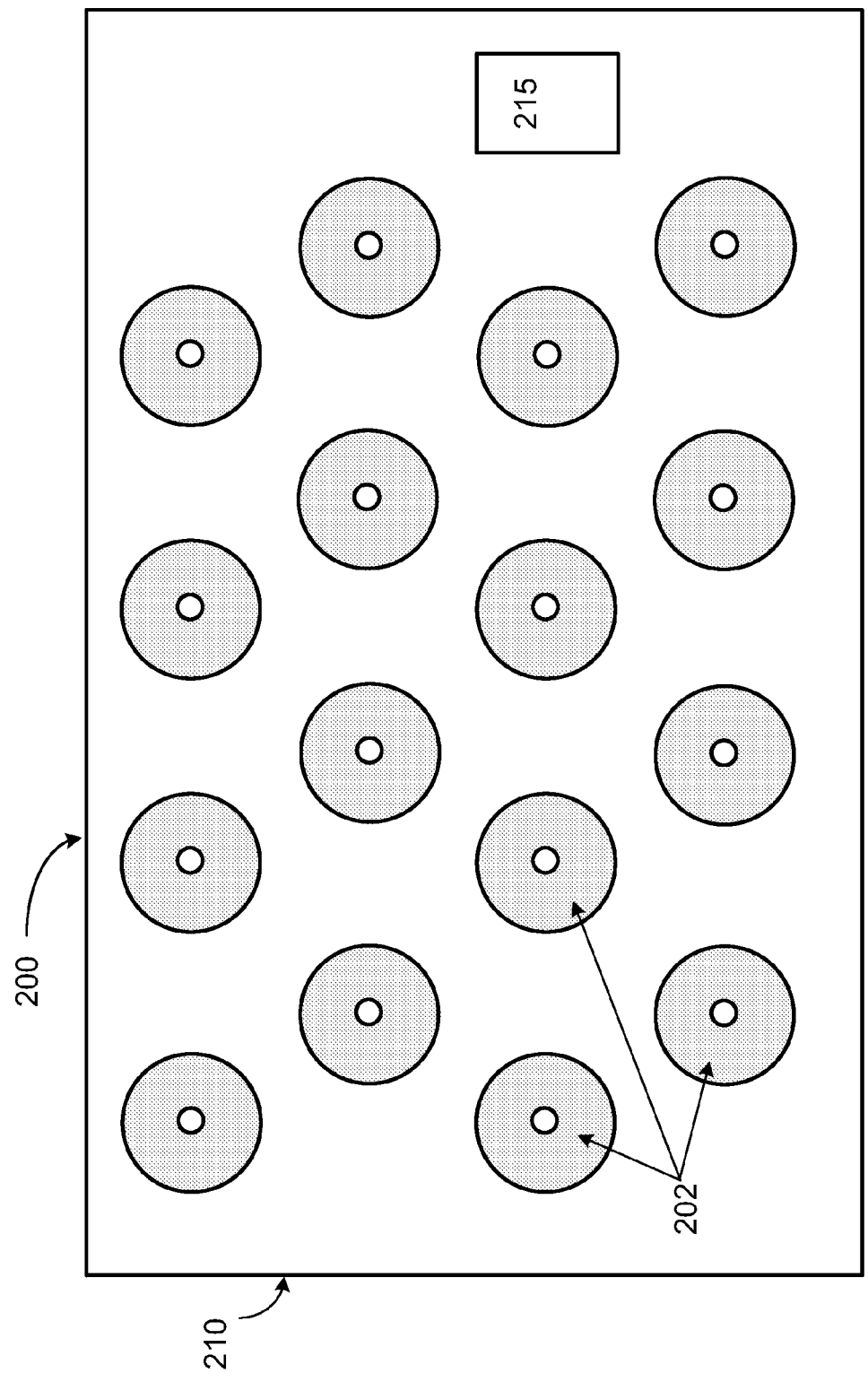
FIG. 2A is a schematic top view of an example of a field generator assembly.

Referring to FIG. 2A, a schematic diagram depicts a top view of an example field generator assembly 200 that includes a plurality of individual field generators 202 (similar to the field generators 108 shown in FIG. 1) distributed on a layer 210. Even though FIG. 2 shows sixteen field generators 202 distributed in a particular manner, this is only for illustrative purposes and should not be considered limiting. More or less number of field generators 202 may be placed in the field generator assembly 200 in various other distributions, including distributions in multiple planes (e.g., vertically distributed planes). The layer 210 can be made of substantially the same material as the covering layer 110 described above with respect to FIG. 1. In some implementations, the layer 210 can be the top surface of a conductive plate or shield (e.g., conductive plate 112 shown in FIG. 1). One or more field generators 202 are connected with each other and to a main power supply by wires (not shown). The connections can be configured in accordance with which generators are scheduled to be simultaneously activated. The field generator assembly 200 may also include a circuit board 215. In some implementations, the circuit board houses an electronic module that controls the excitation or firing of the sets of field generators 202. The circuit board 215 may also include a memory which, in communication with the computing device 106, stores configuration data associated with the field generator assembly 200. The circuit board 215 may also serve as an interface with a power supply powering the field generator assembly 200. In some implementations, the computing device 106 can be implemented as a part of the circuit board 215.

Figure 2B:
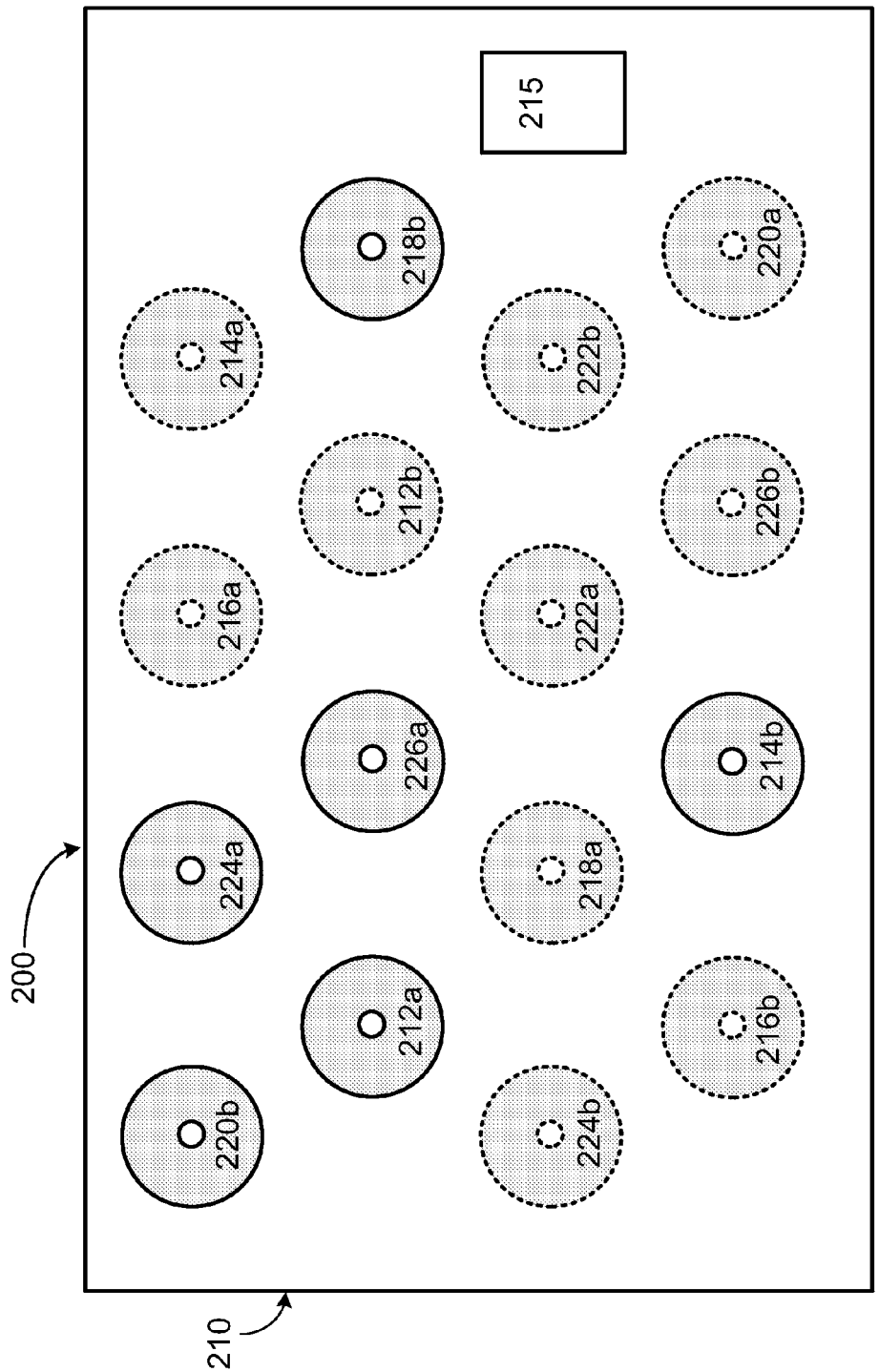
FIG. 2B is a schematic diagram depicting examples of groupings of magnetic field generators in a field generator assembly.

Referring to FIG. 2B, a schematic diagram depicts example groupings of magnetic field generators in a field generator assembly (such as the assembly 200). In this example, the field generators are represented by solid or broken line circumferences to illustrate the direction of current (and therefore the direction of magnetic field induced). In this example, the pairs of generators are grouped for simultaneous activation. For example, the pair of generators 212a and 212b are excited together while the pairs 214a and 214b, 216a and 216b, . . . , 226a and 226b are correspondingly excited together. Generators in a pair being excited together may be provided currents flowing in the same direction thereby resulting in parallel fields. Alternatively, generators in a pair may be provided current flowing in the opposite direction, thereby inducing anti-parallel fields. In the example shown in FIG. 2B, coils having a current flow in one direction are illustrated with solid lines representing their circumferences while coils having a current flow in the opposite direction are illustrated with broken lines. For example, the generators 212a and 212b produce anti-parallel fields while the pair of generators 222a and 222b produce parallel fields. In some implementations, more than two generators may be included in a set being excited together. For example, in some implementations, one set can include the generators 212a, 216a and 214b while another set can include the generators 212a, 218b, 224a and 226b. The location and field orientation of different generators included in a set may depend on the shape of the desired field to be provided by the activated generator pair. Other parameters associated with the generators in a set may also be varied to manipulate the shape of the field induced by the set. Examples of such parameters include distance between the generator coils, orientation of the generator, magnetic flux of the generator (which may be varied by the number of windings or turns, cross section of the coil, nature of the core or current through the coil of the generator) and number of generators in the set.

Referring to FIGS. 2C and 2D, lateral and top views, respectively, of an example of a field generator 227 is shown. The field generator 227 can be designed as a flat coil as shown in these figures. Such relatively thin generators 227 can be used to realize a flat field generator assembly 200 as shown in FIG. 2A. The form factor for such flat field generators can be made to be very thin. For example, the field generator 227 can include two plates 228 housing a coil 229 in between. The plates 228 and the coil 229 can have a common core 230. The diameter 231 of the plates 228 can be, for example, 80 mm and the diameter 232 of the of the coil 229 can be, for example, 60 mm. The thickness 234 of the plates 228 can be made very thin, for example about 1.5 mm, and the thickness of the flat coil can be, for example, about 7 mm. In such cases, the total thickness 238 of the flat field generator can be about 10 mm. The generator 227 can include an orifice 240 in at least one of the plates 228 to allow connection with the coil 229. The diameter 242 of the orifice 240 can be, for example, 3 mm and the diameter 244 of the common core can be 8 mm.

Figure 4A:
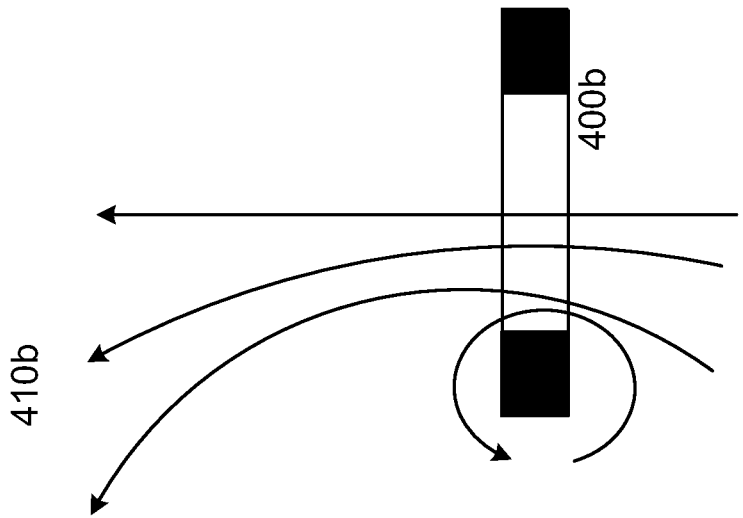
Figure 4A:
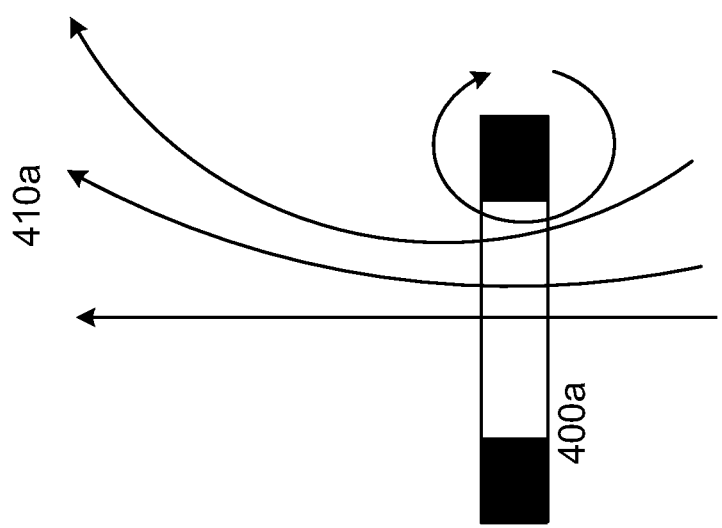
Figure 4B:
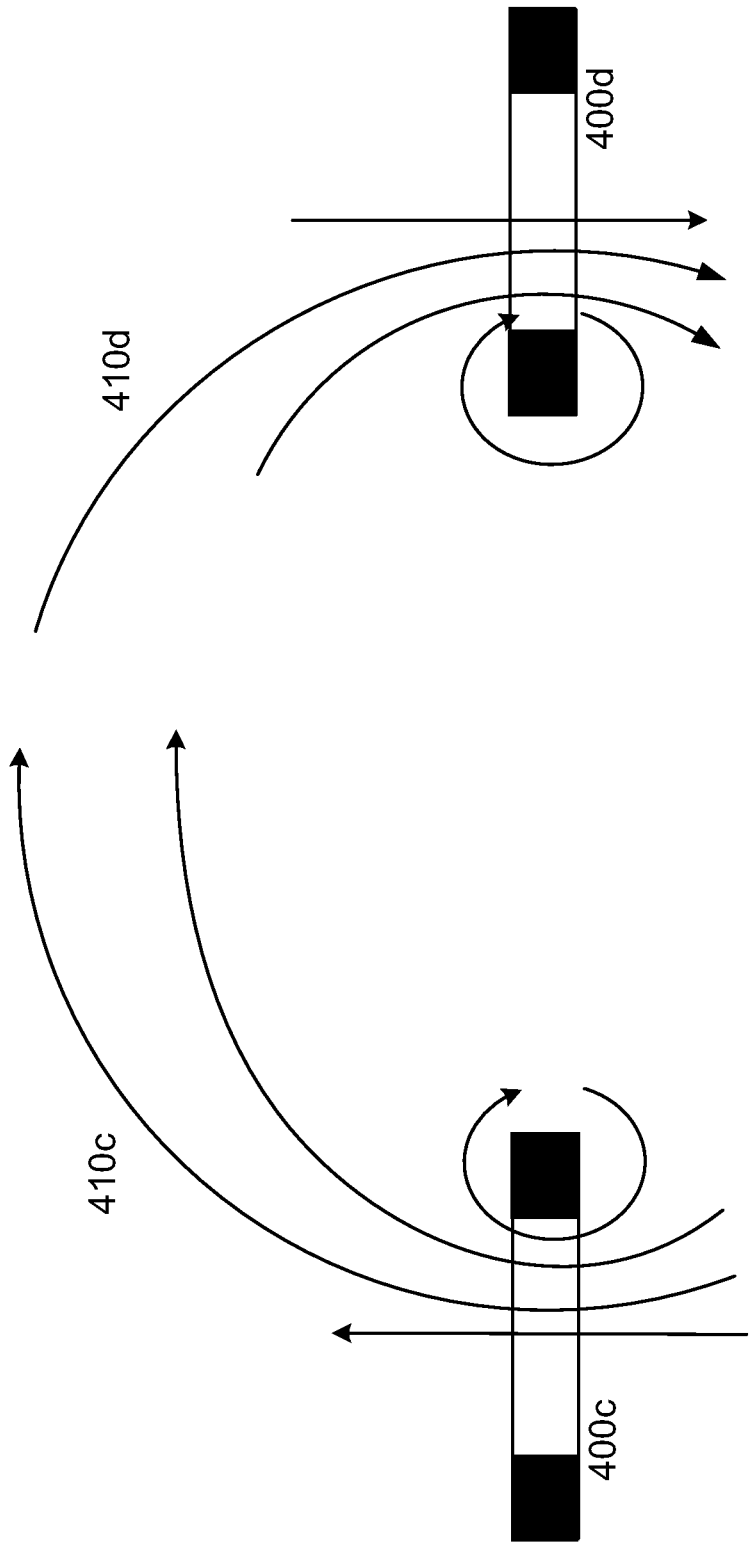

Referring to FIG. 4A, an example of parallel fields induced by a pair of generators 400a and 400b are shown. The current flows in the same direction in both generators 400a and 400b. Therefore the magnetic axes of the generators 400a and 400b are parallel and the resultant magnetic field lines 410a and 410b are mainly vertical. Referring to FIG. 4B, an example of anti-parallel fields induced by a pair of generators 400c and 400d is shown. In this example, the direction of current in one generator 400c is opposite to that in the other generator 400d. Therefore the magnetic axes of the generators 400c and 400d are anti-parallel and the resultant magnetic field lines 410c and 410d are mainly horizontal in the drawing. For such anti-parallel fields, field lines originating from one generator 400c can pass through the other generator 400d. Parameters such as the current, number of windings, and the nature of core in the generators 400a and 400b along with the relative distance and orientation of the generators 400a and 400b can be adjusted to produce a field with a desired shape. In some implementations, generators producing parallel as well as anti-parallel fields may be included in one set to produce the desired shape of magnetic fields.

Referring to FIG. 4C, a field diagram depicts how different sets of generators may act in conjunction with each other and produce magnetic fields of different shapes. In this example, a set of generators including the generators 400a and 400b are activated simultaneously. The pair of field generators 400a and 400b together produce a parallel field 450. A sensor assembly (such as the senor assembly 103) placed in such a field may detect the field and transmit the information to the computing device (such as computing device 106). After a time period (e.g. in the order of milliseconds), the generators 400a and 400b are deactivated and the set including the generators 400c and 400d are activated. The pair 400c and 400d together produce the anti-parallel field 460 which may also be detected and transmitted to a computing device by a sensor assembly. Continuing, several sets of generators may be used to produce magnetic fields of varying shapes and orientations. In some implementations, the sensor assembly detects these different fields and transmits the information to a computing device. In some implementations, the computing device combines the information received from the sensor assembly with information regarding the field generating sources (e.g. information on activation timing and duration, current level, number of windings, number of generators and their relative location etc.) to compute the location of the sensor assembly.

Figure 5:
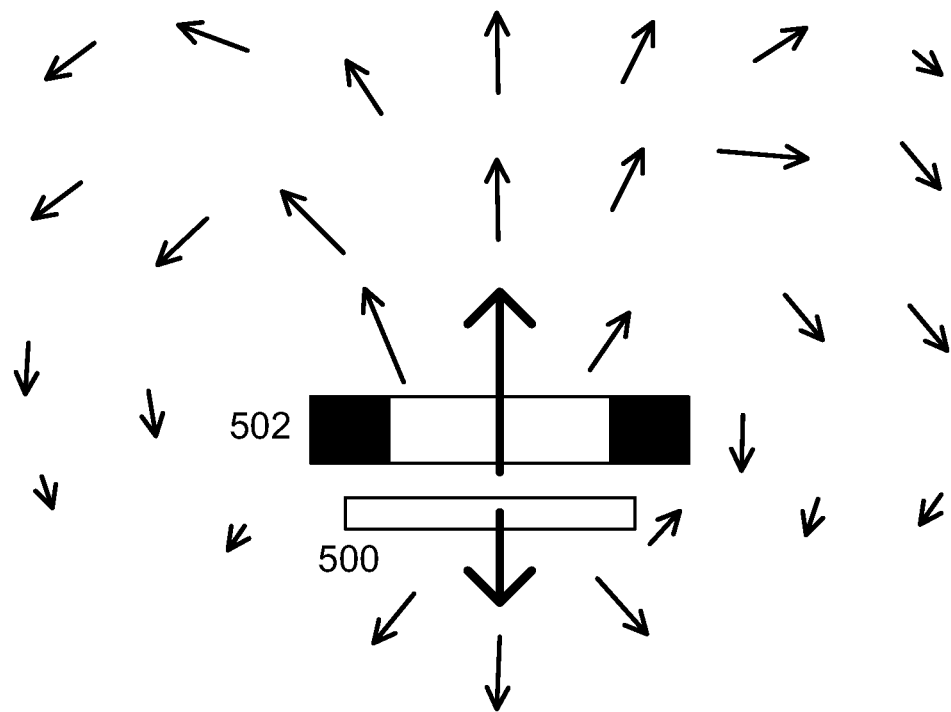
FIG. 5 is a schematic diagram showing an example of a magnetic field induced by a magnetic field generator in the presence of a shield.

Referring to FIG. 5, an example of field shaping using a shield 500 is shown. In some implementations, the shield 500 can be substantially similar to the shield 112 described with reference to FIG. 1. The main field is induced by the generator 502 in which a current flows in a given direction. The induced electromagnetic field gives rise to an eddy current in the shield 500 flowing in a direction opposite to the direction of the current in the generator 502. The shield 500 therefore acts as a second generator where the eddy current induces a field opposing the field due to the generator 502. The interaction of the opposing fields reduces the strength of the field due to the generator 502 in the vicinity of the shield 500. In some implementations, the shield can be configured to reduce the field in its vicinity to strength of nearly zero. Other conducting bodies like a wire loop or a short-circuited coil may also be used in conjunction with the shield 500 (or individually) to shape the magnetic fields produced by a set of generators 502. For example, one or more conducting bodies may be placed in a measurement volume (similar to the region 102 shown in FIG. 1) to change the shape of the generated fields while the shield 500 is used to reduce the strength of the fields below the plane of the field generation assembly. Different types of materials and material shaping may also be used to produce the shield 500. For example, the shield 500 may be frequency selective by incorporating one or more absorption layers or frequency selective layers.

While the system described above makes use of a sensor array to track the tool and the field generator assembly to generate the magnetic fields, it should also be apparent that the inverse of this configuration is equally feasible, i.e. all magnetic sensors could be replaced by generators and all generators replaced by sensors.

Figure 6:
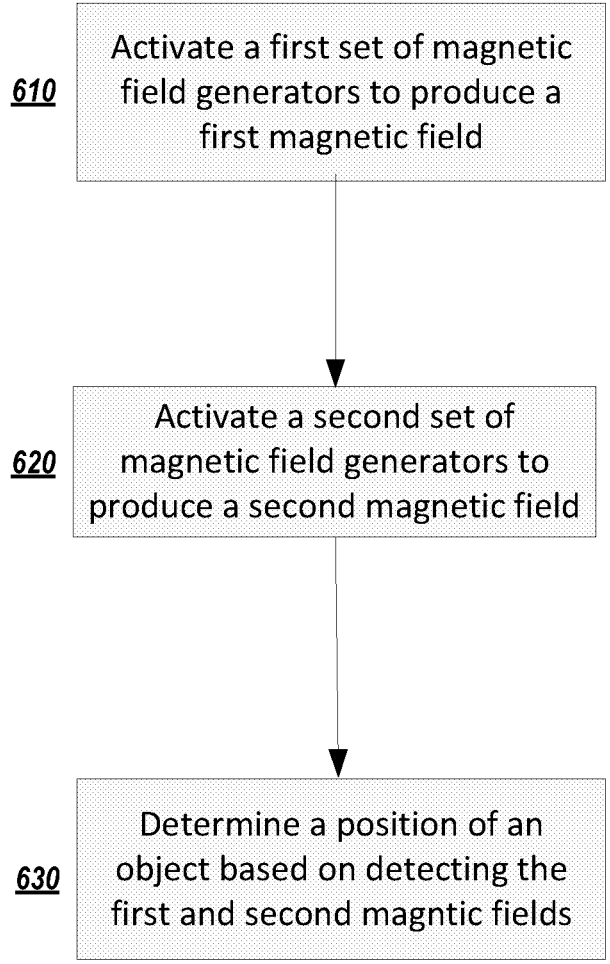
FIG. 6 is a flow chart of an example sequence of operations for controlling the production of magnetic fields and measuring the location of an object.

Referring to FIG. 6, a flowchart 600 shows an example sequence of operations for controlling production of magnetic fields and measuring a location of an object. Operations include activating (610) a first set of magnetic field generators to produce a first magnetic field and activating (620) a second set of magnetic field generators to produce a second magnetic field. Operations also include determining (630) a position of an object based on detecting the first and second magnetic fields.

In some implementations, activating (610) a first set of magnetic field generators include activating two or more individual magnetic field generators simultaneously. The first magnetic field produced by the first set of magnetic field generators is typically a resultant field formed due to super-imposition of individual fields produced by generators in the first set. Some of the generators in the first set can have fields substantially parallel to one another and some of the generators in the first set can have fields substantially anti-parallel to one another. Various parameters of the individual field generators can be adjusted to control the shape of the resultant field. Such parameters include, for example, magnitude of current through a given generator, direction of current through a given generator, relative positions of two or more generators, etc.

Operations also include activating (620) a second set of magnetic field generators to produce a second magnetic field. Activating the second set of generators can be substantially similar to activating the first set of generators. For example, the second magnetic field can also be controlled by adjusting various parameters of the second set including, number of generators, magnitude and/or direction of current in each generator, relative positions of the generators etc. In some implementations, the second set of generators can be activated during a time period when the first set of generators is not activated. Alternatively, the first and second sets may be simultaneously activated, for example, using corresponding activation currents at different frequencies.

Operations also include determining (630) a position of an object based on detecting the first and second magnetic fields. In some implementations, the object can include one or more sensor coils for detecting various parameters of the first and second magnetic fields. For example, the sensor can be configured to detect magnitude and/or orientation of a given magnetic field within a volume. In some implementations, the detected parameters can be related to the position of the object via physical models and equations. As described above with reference to FIG. 1, such physical models and equations can be used to determine the position of the object within the volume. In some implementations, the sensors for detecting the magnetic fields can be at a proximate location with respect to the object.

This written description sets forth the best mode of the invention and provides examples to describe the invention and to enable a person of ordinary skill in the art to make and use the invention. This written description does not limit the invention to the precise terms set forth. Thus, while the invention has been described in detail with reference to the examples set forth above, those of ordinary skill in the art can effect alterations, modifications and variations to the examples without departing from the scope of the invention which is defined by the following claims.

What is claimed is:

1. A magnetic tracking system comprising:
   a field generator assembly generating a plurality of magnetic fields wherein each field is generated by a first set of at least two simultaneously activated magnetic field generators, wherein a magnetic field generated by a first magnetic field generator included in the first set is substantially parallel or substantially anti-parallel to another magnetic field generated by at least a second magnetic field generator included in the first set;
   a magnetic sensor to measure the plurality of magnetic fields; and
   a computing device configured to compute a position and orientation of the magnetic sensor within the magnetic fields being measured by the sensor.

2. The system of claim 1 wherein the magnetic field generators include electromagnetic coils.

3. The system of claim 1 wherein the field generators are positioned on a plane.

4. The system of claim 1 wherein a portion of the magnetic fields generated by the field assembly have different amounts of magnetic flux.

5. The system of claim 1 wherein an eddy current is a source for one of the at least two magnetic field generators.

6. The system of claim 1 wherein one of the at least two magnetic field generators includes a magnetic material.

7. The system of claim 1, wherein the field generator assembly comprises at least a second set of at least two simultaneously activated magnetic field generators, wherein the first set is activated during a first time period and the second set is activated during a second time period, different from the first time period.

8. An apparatus comprising:
   a structural surface for supporting a portion of a patient during a medical procedure; and
   a surface that includes a plurality of magnetic field generator sets for producing magnetic fields to form a measurement volume, wherein each set includes two or more magnetic field generators;
   wherein a magnetic field generated by a first magnetic field generator included in a first magnetic field generator set is substantially parallel or substantially anti-parallel to a magnetic field generated by at least a second magnetic field generator included in the first magnetic field generator set.

9. The apparatus of claim 8, further comprising:
   an electrically conductive layer positioned below the surface that includes the plurality of magnetic field generator sets.

10. The apparatus of claim 8, wherein the plurality of magnetic field generator sets includes a second magnetic field generator set, and wherein the first magnetic field generator set is activated during a first time period and the second magnetic field generator set is activated during a second time period, different from the first time period.

11. A method comprising:
    activating a first set of two or more magnetic field generators to produce a first magnetic field having a first shape within a three dimensional region;
    activating a second set of two or more magnetic field generators to produce a second magnetic field having a second shape within the three dimensional region; and
    determining, a position of a sensor within the three dimensional region based on detecting the first and second magnetic fields by the sensor,
    wherein a magnetic field generated by a first magnetic field generator included in the first set is substantially parallel or substantially anti-parallel to a magnetic field generated by at least a second magnetic field generator included in the first set.

12. The method of claim 11, wherein the first set is activated during a first time period and the second set is activated during a second time period, different from the first time period.

13. A magnetic tracking system comprising:
    a first set of two or more spatially separated magnetic field generators configured to produce a first magnetic field having a first shape within a three dimensional region;
    a second set of two or more spatially separated magnetic field generators configured to produce a second magnetic field having a second shape within the three dimensional region; and
    a computing device configured to compute a position of a sensor within the three dimensional region based on the first and second magnetic fields being detected by the sensor,
    wherein a magnetic field induced by a first magnetic field generator included in the first set of magnetic field generators is substantially parallel or substantially anti-parallel to a magnetic field generated by at least a second magnetic field generator included in the first set of magnetic field generators.

14. The system of claim 13, wherein the field generators from the first set are excited simultaneously to produce the first magnetic field.

15. The system of claim 13, wherein the field generators from the second set are excited simultaneously to produce the second magnetic field.

16. The system of claim 13 further comprising at least a third set of two or more magnetic field generators configured to operate together to form a third magnetic field having a third shape within the three dimensional region, wherein the computing device computes the position of the sensor also based on the sensor detecting the third magnetic field.

17. The system of claim 13 wherein the first and second sets of magnetic field generators are positioned on a common plane.

18. The system of claim 13 wherein the first set of magnetic field generators is activated during a first time period and the second set of magnetic field generators is activated during a second time period, different from the first time period.

19. The system of claim 13 wherein the first and second sets of magnetic field generators are active during a first time period.

20. The system of claim 13 wherein the first set of magnetic field generators operate at a first frequency and the second set of magnetic field generators operate at a second frequency, different from the first frequency.

* * * * *